United States Patent [19]

Nickolls et al.

[11] Patent Number: 5,181,511
[45] Date of Patent: Jan. 26, 1993

[54] APPARATUS AND METHOD FOR ANTITACHYCARDIA PACING USING A VIRTUAL ELECTRODE

[75] Inventors: Peter Nickolls, Vaucluse, Australia; Richard M. T. Lu, Aurora, Colo.; Kenneth A. Collins, Neutral Bay, Australia; Roy M. McCulloch, Cherrybrook, Australia; Lucy M. Cheatle, Lane Cove; Brian Cleland, Warrawee, all of Australia

[73] Assignee: Telectronics Pacing Systems, Inc., Englewood, Colo.

[21] Appl. No.: 780,753

[22] Filed: Oct. 21, 1991

[51] Int. Cl.⁵ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,857,398 | 12/1974 | Rubin | 128/419 D |
| 3,942,534 | 3/1976 | Allen et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,429,697 | 2/1984 | Nappholz et al. | 128/419 PG |
| 4,869,252 | 9/1989 | Gilli | 128/419 PG |
| 4,940,054 | 7/1990 | Grevis et al. | 128/419 PG |
| 4,998,974 | 3/1991 | Aker | 128/419 PG |

OTHER PUBLICATIONS

F. E. Marchlinski et al., "Prevention of Ventricular Tachycardia Induction During Right Ventricular Programmed Stimulation By High Current Strength Pacing At The Site of Origin"; *Circulation*, vol. 76, No. 2, pp. 332-342.

M. E. Josephson et al., "Electrophysiologic Basis For Sustained Ventricular Tachycardia-Role of Reentry"; *Tachycardias: Mechanisms, Diagnosis, Treatment*, publ. by Lea & Febiger, Philadelphia, 1984, Chapter 14, pp. 305-323.

J. D. Fisher et al., "Termination of Ventricular Tachycardia With Bursts of Rapid Ventricular Pacing", *American Journal of Cardiology*, vol. 41, pp. 94-102 (Jan. 1978).

*Primary Examiner*—Lee S. Cohen
*Assistant Examiner*—Jeffrey R. Jastrzab
*Attorney, Agent, or Firm*—Gottlieb, Rackman & Reisman

[57] ABSTRACT

An implantable device and method for treating cardiac arrhythmias in a patient's heart are disclosed. A source of antitachycardia pacing therapy and an electrode system including at least three electrodes for delivering the antitachycardia pacing therapy to the heart are provided. Circuitry and software for detecting a tachycardia having a site of focus in the heart and for determining the relative distances of the electrodes from the focus site are also provided. The three or more electrodes are connected to the source of antitachycardia pacing therapy based on the relative distances determined and in such a manner as to create a virtual electrode at the focus site upon delivery of the therapy to the heart.

28 Claims, 6 Drawing Sheets

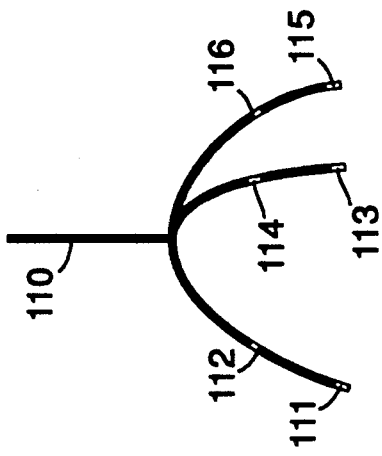
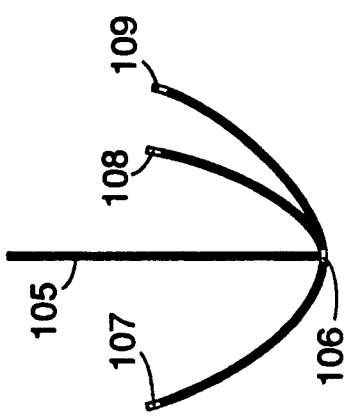
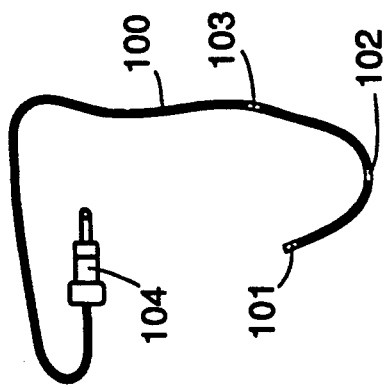
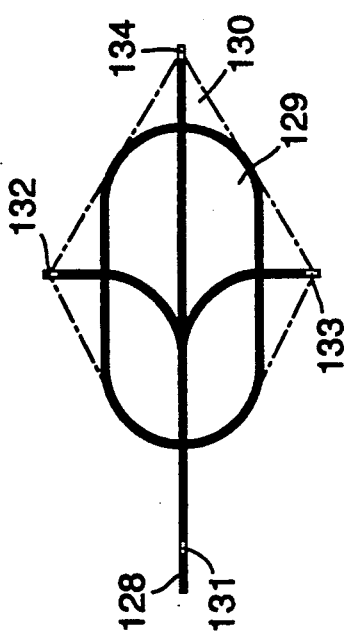
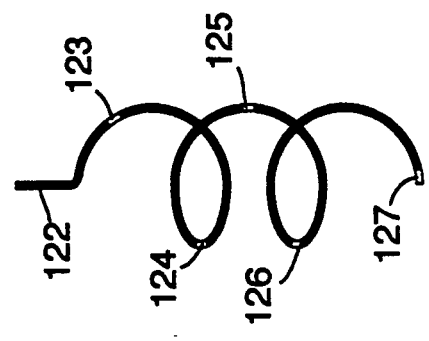
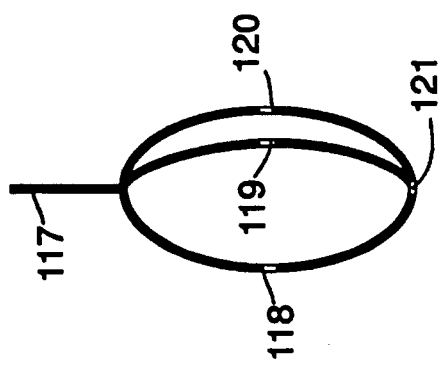

APPARATUS AND METHOD FOR ANTITACHYCARDIA PACING USING A VIRTUAL ELECTRODE

TECHNICAL FIELD

This invention relates to implantable medical devices which monitor the cardiac state of a patient by sensing the patient's intrinsic rhythm, atrial and ventricular tachycardia and atrial fibrillation/flutter and which deliver therapy in the form of electrical energy to cardiac tissue in both chambers of the right heart in an attempt to revert tachycardia and restore a normal sinus rhythm. More particularly, the invention relates to an apparatus and method for antitachycardia pacing in a dual chamber arrhythmia control system. Although the invention may be incorporated into an antitachycardia device alone, it is described herein as operating in a combined implantable antitachycardia pacing, bradycardia pacing, defibrillating or cardioverting arrhythmia control system.

As used herein, the term "tachycardia" refers to any fast abnormal rhythm of the heart which may be amenable to treatment by electrical discharges and specifically includes supraventricular tachycardia (SVT), atrial tachycardia (AT), atrial flutter and atrial fibrillation (AF), ventricular tachycardia (VT), ventricular flutter and ventricular fibrillation (VF). The term "ATP" refers to antitachycardia pacing.

U.S. Pat. No. 3,857,398 to Rubin, entitled "Electrical Cardiac Defibrillator," describes a combined pacer/defibrillator. This device either performs a bradycardia pacing or a defibrillation function depending on the detection of a VT/VF. If a VT/VF is detected, the device is switched to the defibrillating mode. After a period of time to charge the capacitor, a defibrillation shock is delivered to the patient.

Improvements to this device were contained in a multiprogrammable, telemetric, implantable defibrillator which is disclosed in Co-pending U.S. patent application Ser. No. 576,178, filed Aug. 29, 1990, entitled "Reconfirmation Prior to Shock for Implantable Defibrillation." This device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached.

As cardioversion or defibrillation shocks can be very unpleasant to a patient, especially when delivered frequently, it became necessary to provide a device which included antitachycardia pacing therapy along with bradycardia support pacing therapy and defibrillation or cardioversion therapy, so that the implanted device could automatically provide the necessary therapy from a range of therapies offered by the device. Hence a further development in the field of combined implantable devices is described in U.S. Pat. No. 4,940,054 to Grevis et al., entitled "Apparatus and Method for Controlling Multiple Sensitivities in Arrhythmia Control System Including Post Therapy Pacing Delay." The above device is a microcomputer-based arrhythmia control system which is programmable by means of a telemetric link. The device provides single chamber bradycardia support pacing, antitachycardia pacing, and cardioversion or defibrillation shocks for restoring normal sinus rhythm to a patient.

Additionally, various specific developments have been made in the field of tachycardia control pacers. Tachycardia is a condition in which the heart beats very rapidly, from 100 bpm and typically about 150 bpm. There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback of an electrical stimulus which prematurely triggers another beat. By interposing a stimulated heartbeat, the stability of the feedback loop is disrupted.

In U.S. Pat. No. 3,942,534 to Allen et al., entitled "Device for Terminating Tachycardia," there is disclosed a pacer which, following detection of a tachycardia, generates an atrial (or ventricular) stimulus after a delay interval. If that stimulus is not successful in terminating the condition, then another stimulus is generated after another premature heartbeat following a slightly different delay. The device constantly adjusts the delay interval by scanning through a predetermined delay range. Stimulation ceases as soon as the heart is restored to sinus rhythm. If successful reversion is not achieved during one complete scan, then the cycle is repeated. The device further provides a second stimulus following the first, i.e., before the next naturally occurring rapid beat. The time period between a heartbeat and the first stimulus is known as the initial delay, while the time period between the first stimulus and the second stimulus is known as the coupled interval. In the above device, once the coupled interval is set by a physician it is fixed, and therefore the second stimulus always occurs a predetermined time after the first stimulus, no matter when the first stimulus occurs after the last heartbeat or how fast is the rate of the tachycardia.

In U.S. Pat. No. 4,390,021 to Spurrell et al., entitled "Two Pulse Tachycardia Control Pacer," there is disclosed a pacer for controlling tachycardia in which the coupled interval is scanned in addition to the initial delay. The time parameters which are successful in terminating the tachycardia are stored so that upon confirmation of another tachycardia event, the previously successful time parameters are the first ones to be tried. The device also allows tachycardia to be induced by the physician to allow for programming of the initial delay and the coupled interval parameters.

U.S. Pat. No. 4,398,536 to Nappholz et al., entitled "Scanning Burst Tachycardia Control Pacer," discloses a scanning burst tachycardia control pacer wherein, following each tachycardia confirmation, a burst of a programmed number of stimulating atrial (or ventricular) pulses is generated. The rates of the bursts increase from cycle to cycle whereby following each tachycardia confirmation, a pulse burst at a different rate is generated. The rate of a burst which is successful in terminating tachycardia is stored, and following the next tachycardia confirmation, the stored rate is used for the first burst which is generated.

In U.S. Pat. No. 4,406,287 to Nappholz et al., entitled "Variable Length Scanning Burst Tachycardia Control Pacer," there is disclosed a variable length scanning burst tachycardia control pacer. The physician programs the maximum number of pulses in a burst. The number of pulses in a burst is scanned, and the number which is successful in terminating tachycardia is registered so that it is available for first use when a new tachycardia episode is confirmed. Successive bursts, all at the same rate, have different numbers of pulses, the pulse number scanning being in the upward direction. If all bursts are unsuccessful, a new rate is tried and the number scanning begins over again. Thus, all combinations of rates and pulse numbers are tried, with the successful combination being used first following the next tachycardia confirmation.

U.S. Pat. No. 4,408,606 to Spurrell et al., entitled "Rate Related Tachycardia Control Pacer," discloses a rate-related tachycardia control pacer wherein, following tachycardia confirmation, a burst of at least three stimulating pulses is generated. The time intervals between successive pulses decrease by a fixed decrement, hence the rate of the pulses increases during each cycle of operation. The first pulse is generated following the last heartbeat which is used to confirm tachycardia at a time which is dependent on the tachycardia rate. The time delay between the last heartbeat and the first pulse in the burst is equal to the time interval between the last two heartbeats less the fixed decrement which characterizes successive time intervals between stimulating pulses.

It is known that the detection of a ventricular beat or the generation of a ventricular pacing pulse initiates the timing of an interval known as the VA delay. Dual chamber heart pacers have been developed in order to generate sequential atrial and ventricular pacing pulses which closely match the physiological requirements of the patient. A conventional dual chamber heart pacer is disclosed in U.S. Pat. No. 4,429,697 to Nappholz et al., entitled "Dual Chamber Heart Pacer With Improved Ventricular Rate Control." It includes atrial beat sensing and pulse generating circuits along with ventricular beat sensing and pulse generating circuits. If an atrial beat is not sensed prior to expiration of the VA delay interval, then an atrial pacing pulse is generated. Following the generation of an atrial pacing pulse, or a sensed atrial beat, an interval known as the AV delay is timed. If a ventricular beat is not sensed prior to the expiration of the AV delay interval, then a ventricular pacing pulse is generated. With the generation of a ventricular pacing pulse, or the sensing of a ventricular beat, the VA delay timing starts again. This patent describes how the VA delay timing interval may be divided into three parts—the atrial refractory period, the Wenckeback timing window, and the P-wave synchrony timing window. It outlines the importance of controlling the ventricular rate in comparison with the atrial rate in order to maintain synchrony between the atrium and the ventricle. The patent does not however address the issue of antitachycardia pacing therapy.

Prior art single chamber antitachycardia pacing devices which provide antitachycardia pacing bursts to either the atrium or the ventricle have shortcomings in that they lack the required synchrony between the atrium and the ventricle. This reduces the percentage of successful reversions. Although ventricular antitachycardia pacing in particular may revert an arrhythmia, it increases the risk of adversely affecting the patient by means of a decrease in arterial pressure due to the rapid pacing. As a result of the haemodynamic compromise or lowered haemodynamic status of the myocardium during the arrhythmia and pacing, there is a high risk that a ventricular tachycardia will accelerate to a faster ventricular tachycardia, and even to a ventricular fibrillation. This has been shown in an article by Fisher et al., entitled "Termination of Ventricular Tachycardia with Bursts of Rapid Ventricular Pacing," appearing in American Journal of Cardiology, Vol. 41, pages 94-102 (January, 1978). Not only does this present a potentially hazardous situation to the patient, but it also makes it more difficult for the device to revert the patient. Reversion would necessarily demand more energy of the device and perhaps even cardioversion or defibrillation therapy, which is not available in many pacing devices. Furthermore, prior art devices have been limited in the provision of individualized therapy to the patient by patient-dependent parameters such as the AV delay.

In U.S. Pat. No. 4,998,974 to N. L. Gilli, entitled "Apparatus and Method for Antitachycardia Pacing in Dual Chamber Arrhythmia Control System," which patent is assigned to the assignee of the present invention, the AV delay is programmable as a percentage of the tachycardia cycle length in order to improve the synchrony between the atrium and the ventricle during antitachycardia pacing therapy.

Antitachycardia pacing has been used as a therapy since the mid-seventies with pacing stimuli being delivered from an implantable pulse generator. Many organized tachyarrhythmias are susceptible to termination by antitachycardia pacing, although all forms of fibrillation are immune. The patient groups treated include those with supraventricular tachyarrhythmias and ventricular tachyarrhythmias. However, due to the possible risk of antitachycardia pacing therapy either accelerating the arrhythmias or precipitating ventricular fibrillation, changes in the manner in which this therapy is employed in the pulse generator in recent years has resulted in a safer and more effective antitachycardia therapy.

One of the mechanisms which has been believed to cause tachycardias is reentry. Reentrant tachycardias depend on two alternative pathways with differing conduction and refractoriness properties. The initiation of a tachycardia occurs when a premature wave front arrives at the potential reentry circuit and finds one of the two potential pathways unable to conduct (unidirectional block). Premature beats, impinging on the relative refractory period, are conducted slowly around the circuits, and if sufficient time has elapsed (balance between conduction velocity and refractory period in the circuit), the wave front will continue around (reenter the circuit), maintaining the tachycardia. Termination of tachycardia occurs when a premature beat cannot enter the circuit in the same direction as the tachycardia wave front because of refractoriness, but can enter the circuit in the opposite direction, ultimately colliding with the advancing wave front and extinguishing it. The timing of the premature beat that is able to terminate the tachycardia (the termination zone or window during the cardiac cycle) is dependent on the properties both of the circuit and of the myocardium between the circuit and the point of origin of the premature beat. A relatively wide termination zone is favored by the following: a short distance or rapid conduction in the myocardium outside the circuit; a large circuit; or slow conduction with moderate refractoriness within the circuit.

Although current technology allows the integration of antitachycardia pacing with defibrillation therapy in the same device, the discomfort due to the delivery of high energy shocks to the heart can be avoided and the life of such a device can be lengthened if the effectiveness of antitachycardia pacing therapy can be improved.

Many antitachycardia pacing therapy devices at present include defibrillation support within the device in order to provide adequate safety to a patient. It is highly advantageous to prevent the development of VT's or atrial fibrillations, and to terminate them quickly if they appear, rather than allowing the arrhythmia to develop to such an extent that a defibrillation shock is necessary.

Despite the sophistication of antitachycardia pacing (ATP) algorithms used in existing devices, an important consideration has heretofore been overlooked, namely the distance between the pacing site and the site of origin of a tachycardia. This is recognized in an article by Marchlinski et al., entitled "Prevention of Ventricular Tachycardia Induction During Right Ventricular Programmed Stimulation by High Current Strength Pacing at the Site of Origin," appearing in Circulation, Vol. 76, No. 2, pages 332-342 (August, 1987).

Furthermore, it has been found that many tachycardias arise in the left ventricle. It is not possible to place electrodes in the left ventricle permanently. So, if a rapid tachycardia develops at this site, it will not be possible to terminate it by ATP therapy delivered through a single electrode in the right ventricle due to the distance of the stimulating electrode from the site of origin of the VT.

Chapter 14 of the book "Tachycardias: Mechanisms, Diagnosis, Treatment," authored by Josephson and Wellens and published by Lea & Febiger, Philadelphia (1984), discloses that in some patients single stimuli from the right ventricular outflow tract can terminate tachycardias when triple extrastimuli from the right ventricular apex fail to do so. It further discloses that only rarely can stimulation from the right ventricle be more effective than that from the left ventricle in terminating ventricular tachycardia.

Additionally, in present devices even with quite effective ATP algorithms, many arrhythmias still cannot be terminated because of their rapid nature since the time taken for the arrhythmia wavefront to recirculate is less than the time taken for the ATP therapy pulse train to travel from the stimulating electrode to the site of the arrhythmia. In general tachyarrhythmias with a cycle length <230-250 ms are difficult to terminate by ATP for this reason.

It is therefore an object of the present invention to identify endocardially the direction of the depolarization wavefront arising from the site of origin of a ventricular tachycardia.

It is further object of the invention to provide successful ATP termination of such tachycardia by creating a virtual electrode at a point closer to or at the site of origin of the tachycardia. As used herein, the term "virtual electrode" refers to an electric field the strength of which is above the stimulation threshold of adjacent cardiac tissue. For a particular VT, a virtual electrode is created by applying suitable voltages to two or more electrodes, and a zero voltage to a reference electrode.

It is another object of the invention to provide active electrodes strategically positioned around the focus of the VT, for example in the right ventricle, subcutaneously over the heart and on the left epicardial surface of the heart, with a reference electrode placed at a distance. Therefore, when suitable voltages are applied, an electric field is created in the vicinity of the tachycardia focus, the strength of which is above the stimulation threshold for the myocardial tissue. Depending on the positioning and impedance of the active and reference electrodes, the stimulating pulse amplitude may need to be as high as 15 V. Conventional trains of pulses may be used, such as automatic decrementing or incrementing orthogonal bursts.

It is a still further object of the invention to provide improved, reliable ATP therapy with a higher chance of faster and more successful reversion.

It is yet another object of the invention to provide more effective single and dual chamber antitachycardia pacing systems which reduce the number of or the necessity for defibrillation shocks to be given to a patient by preventing the development of VF's and AF's in a patient.

Briefly stated, and in accordance with one aspect of the invention, there is provided a single or dual chamber antitachycardia pacing device, in an automated arrhythmia control system including a pacemaker and a plurality of electrodes, in which the electrodes are used as sensors to determine which of the electrodes are nearest to the site of the tachycardia. The selected electrodes are then used to create the required virtual electrode. The selected electrodes are given peak voltages higher than the stimulation threshold of the tissue in the area of the tachycardia focus site in order to provide ATP therapy thereto. The ATP therapy is in the form of simultaneous pacing waves which approach the focus site from different directions, effectively from all sides if the selected electrodes surround the site, otherwise from a point or line or area near the site. In a preferred embodiment of the invention the electrodes nearest the site of the tachycardia are found by identifying fiducial points on the intracardiac electrogram (ICEG) waveform, such as peaks, points of maximum positive or negative slope and inflections, and examining the relative timing of these points. The electrodes nearest the focus of the arrhythmia will have fiducial points in the ICEG appearing earliest.

DETAILED DESCRIPTION

Figure 1:
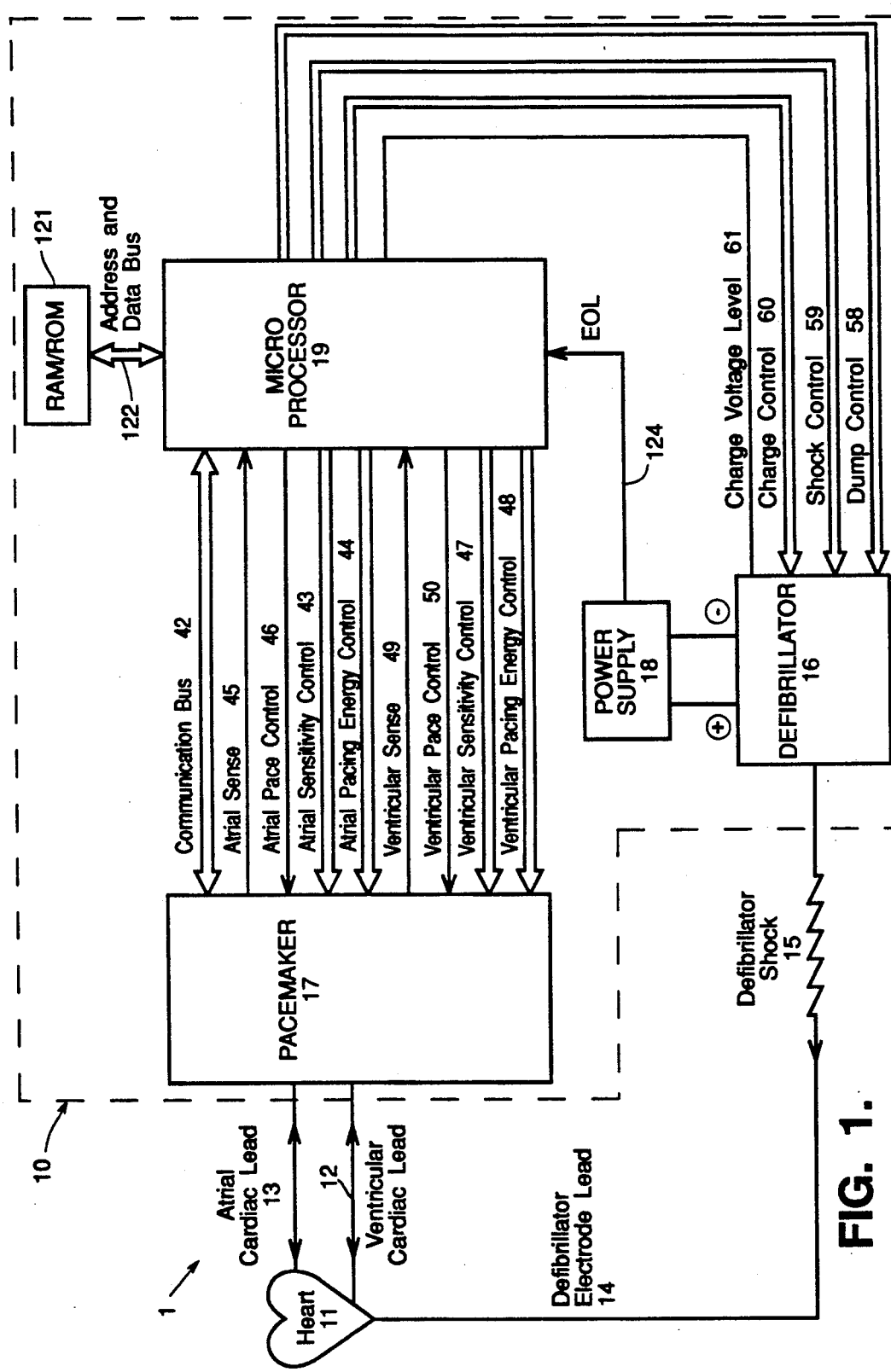
FIG. 1 is a block diagram of a dual chamber arrhythmia control system (ACS) in accordance with the present invention.

Referring to FIG. 1, there is depicted a block diagram of a dual chamber arrhythmia control system, shown generally at 1. System 1 is designed to be implantable in a patient and includes a cardioverter/defibrillator pacemaker or pulse module, shown generally at 10, and appropriate leads for connecting module 10 to a patient's heart 11. More particularly, system 1 will generally include an atrial cardiac lead 13 extending to the atrium of the patient's heart for the administration of therapy to the atrium, and a ventricular cardiac lead 12 extending to the ventricle of the patient's heart for the administration of therapy to the ventricle. System 1 generally also includes a pacemaker 17 for the detection of analog signals representing cardiac electrical activity and for the delivery of bradycardia or antitachycardia pacing pulses to both chambers of the heart; a microprocessor 19 which, in response to various inputs received from the pacemaker 17 as well as from a defibrillator 16, performs various operations so as to generate different control and data outputs to both the pacemaker 17 and the defibrillator 16; and a power supply 18 for the provision of a reliable voltage level to pacemaker 17, microprocessor 19, and defibrillator 16. Defibrillator 16 produces a high voltage to charge its capacitors and then optionally discharges them in response to control signals from microprocessor 19. A defibrillator electrode lead 14 transfers the energy of a defibrillator shock 15 from the implanted pulse module 10 to the surface of the heart 11. By way of definition for the arrhythmia control device as a whole, the term "cardioversion" as used herein refers to the discharge of electrical energy into cardiac tissue in an attempt to terminate or revert a tachycardia. The energy discharge may range from a high of 40 Joules or more to a low of less than 1 Joule. The discharge may be monophasic or biphasic but is not restricted to these waveforms. Cardioversion shocks may or may not be synchronized to the rhythm of the heart. Defibrillation is a particular example of cardioversion. Also, the invention applies equally to devices which deliver energy synchronized to a P- or an R-wave and to those that do not, and it applies to devices which use lower energy pulses (up to 1 Joule) as well as to devices which use greater energy pulses (up to 40 Joules or more).

Microprocessor 19 is connected to a random access memory/read only memory (RAM/ROM) unit 121 by an address an data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48. As also more fully described below, microprocessor 19 is connected to defibrillator 16 by a charge voltage level line 61, a charge control bus 60, a shock control bus 59, and a dump control bus 58.

Figure 2:
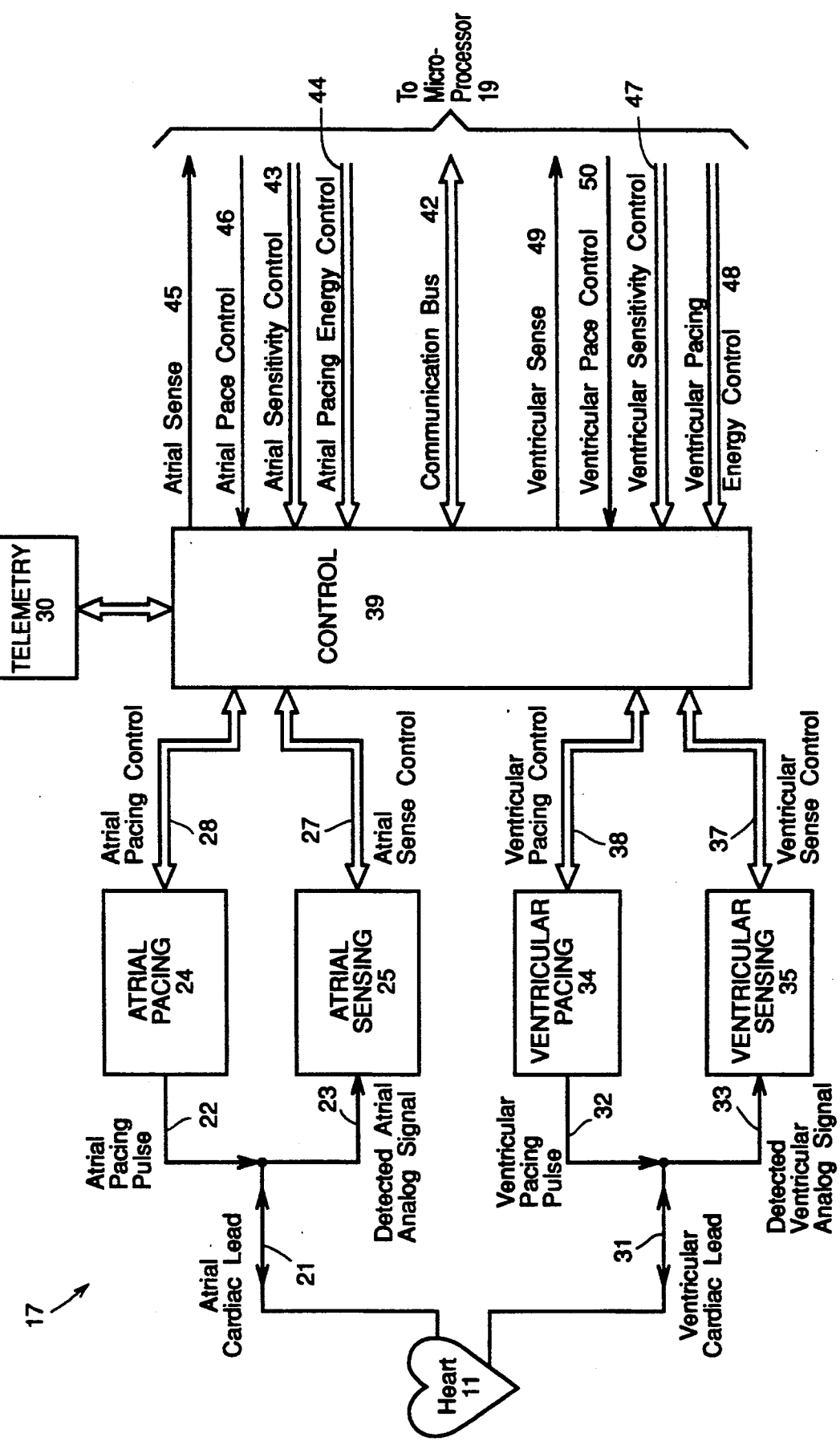
FIG. 2 is a block diagram of a pacemaker employed in the ACS of FIG. 1.

Referring to FIG. 2, there is depicted a block diagram of the pacemaker 17 of FIG. 1. As seen therein, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuits. A change in this sensitivity will affect the voltage deviation required at the sensing electrode for a sense to be registered. The operation of the logic which changes the sensitivity is described in more detail in U.S. Pat. No. 4,940,054 to Grevis et al., entitled "Apparatus and Method for Controlling Multiple Sensitivities in Arrhythmia Control System Including Post Therapy Pacing Delay," which description is incorporated herein by reference.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in more detail in U.S. Pat. No. 4,869,252 to N. L. Gilli, entitled "Apparatus and Method for Controlling Pulse Energy in Antitachy-arrhythmia and Bradycardia Pacing Devices," which description is incorporated herein by reference. The pacing circuitry 24 and 34 generate atrial pacing pulses (or bursts of pulses for antitachycardia pacing) 22 and the ventricular pacing pulses (or bursts of pulses for antitachycardia pacing) 32 which are delivered to the patient's heart 11 by means of the atrial cardiac lead 21 and the ventricular cardiac lead 31.

Telemetry circuitry 30 provides a bi-directional link between control block 39 and an external device such as a programmer. It allows data such as the operating parameters to be read from or altered in the implanted module 10 (FIG. 1).

Figure 3:
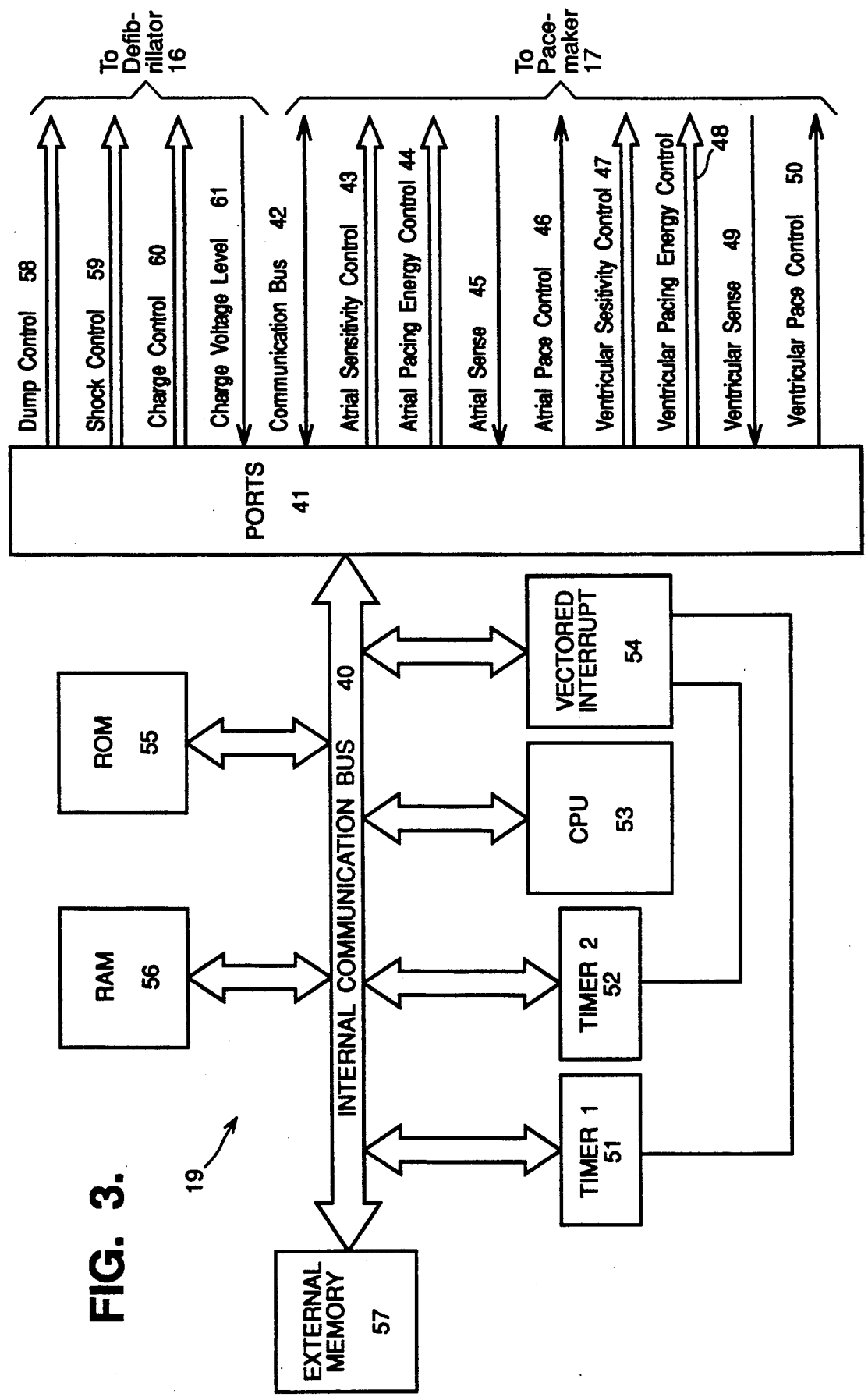
FIG. 3 is a block diagram of a microprocessor employed in the ACS of FIG. 1.

Referring to FIG. 3, there is shown a block diagram of the microprocessor 19 of FIG. 1. It comprises two 16-bit timers 51 and 52, a CPU 53, a vectored interrupt block 54, a ROM 55, a RAM 56, an external memory 57, a ports block 41 and an internal communication bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic employed by the module 10, as well as storage programs for storing, in external memory 57, data concerning the functioning of module 10 and the electrograms provided by cardiac leads 12 and 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communication bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communication bus 42, through control block 39 in pacemaker 17, and into telemetry circuit 30 for transmission to the external programmer by a transmitter in telemetry circuit 30.

Microprocessor 19 receives various status and/or control inputs from pacemaker 17 and defibrillator 16, such as the sense signals on lines 45 and 49. It performs operations such as arrhythmia detection, and produces outputs such as the atrial pace control on line 46 and the ventricular pace control on line 50 which determine the type of pacing to take place. Other control outputs generated by the microprocessor 19 include the atrial and ventricular pacing energy controls on buses 44 and 48, respectively, which determine the magnitude of the pulse energy, the shock control on bus 59 which signals that a shock is to be delivered to the patient. The device may include the optional feature of a dump control on bus 58 which indicates that a shock is to be dumped at an internal load within the defibrillator. The charge control on bus 60 determines the voltage level of the shock to be delivered, and the atrial and ventricular sensitivity controls on buses 43 and 47 determine the sensitivity setting of the sensing circuits. Charge voltage level line 61 provides a digital signal representative of charge voltage from an analog-to-digital converter within defibrillator 16, thus providing a feedback loop which assures that a shock of proper energy level is delivered by defibrillator 16.

In the automated system of the present invention, the pacemaker uses multiple distal electrodes on atrial lead(s) 13 (FIG. 1) and ventricular lead(s) 12 as sensors to determine which of the electrodes are closest to the site of the tachycardia. These electrodes are then used to create the required virtual electrode. Such sensing is accomplished by simply measuring the time differentials between fiducial points on the QRS complexes of the tachycardia recorded at each electrode. Those electrodes whose fiducial points appear earliest are electrically closest to the focus of the arrhythmia. The two or three closest are then used for ATP. The fiducial points are the positive or negative peaks of the complex and its derivative. In each case the point of largest magnitude is taken as the fiducial point.

During ATP, the pacing electrodes will all have peak voltages greater than the tissue threshold voltage applied to them. Accordingly, the pacing stimuli can appear over a larger area than the nominal virtual electrode site. This does not present any problems, however. In fact it is likely to provide a more effective means of therapy with simultaneous pacing waves approaching the focus site from all sides.

Figure 4:
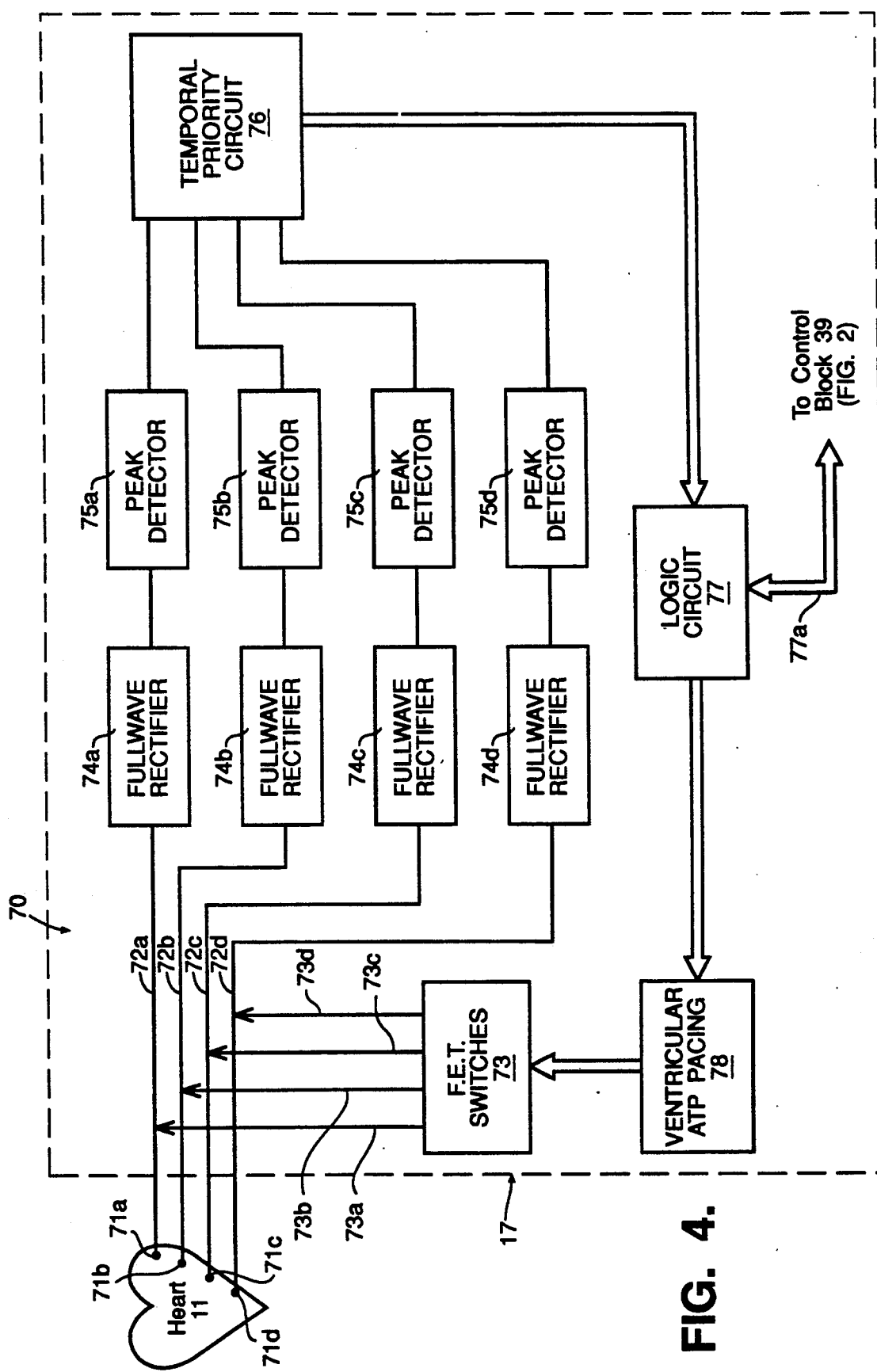
FIG. 4 is a circuit diagram showing the operation of a sensing circuit utilized in the ACS of FIG. 1, which circuit enables the identification of a VT focus and the establishment of a virtual electrode.

Referring to FIG. 4 a sensing circuit, shown generally at 70, is provided within pacemaker 17 for determining the relative distances of the various sensing electrodes from the site of the focus of a tachycardia. In the embodiment shown in FIG. 4, four electrodes, shown diagrammatically at 71a, 71b, 71c and 71d, are placed at a number of sites within and around the patient's heart 11, preferably in the ventricle, but in an alternative embodiment also in the atrium. These electrodes correspond to the electrodes carried by ventricular cardiac lead 12 of FIG. 1 in the preferred embodiment, and to those carried by leads 12 and 13 in the alternative embodiment. Signals from electrodes 71a-71d pass along corresponding leads 72a, 72b, 72c and 72d to the pacemaker 17. They first pass through respective FET switches 73a-73d of an FET switch block 73 and then to respective full wave rectifiers 74a-74d and respective peak detectors 75a-75d. The purpose of these circuits is to find a fiducial point on each of the signals, such as the peak, and the time at which this fiducial point occurs, in order to determine the chronological order of the signals. As an alternative, comparators (not shown) can be used instead of rectifiers 74a-74d and detectors 75a-75d to determine when there are zero crossing or when the signals pass particular thresholds, or differentiator/highpass filters (not shown) can be used to find the points of maximum slope. A temporal priority circuit 76 is used to determine the chronological order of the fiducial points of the separate input signals for each heart beat.

Those electrodes which are electrically closest to the focus of a tachycardia will produce signals whose fiducial points appear at the earliest points in time. These are the electrodes which can then be used to deliver ATP therapy. Knowing the physical (geographical) distribution of the electrodes, which information is programmed into the pacemaker 17 and delivered to a logic circuit 77 from control block 39 thereof via a line 77a, and knowing the chronological order of their signals, the relative site of the focus of the tachycardia can then be determined by logic circuit 77. The logic circuit thus selects those electrodes which are near to or surround the focus. The logic circuit then uses the FET switches 73a-73d, which are arranged as cross bar switch circuits, to connect ventricular ATP pacing circuits 78 to the appropriate electrodes. The logic circuit 77 also controls the output amplitudes and phases of the ventricular ATP pacing circuit 78 in order to create the appropriate virtual electrode field as close as possible to the tachycardia focus. The ventricular ATP pacing circuit 78 may deliver any type of currently used ATP therapy.

When a tachycardia is detected by the pacemaker 17, for example by interval discrimination and/or morphology analysis, the sensing circuit 70 determines which of the sensing electrodes are closest to the site of focus of the tachycardia, and switches FET's in its output so as to connect an appropriate orientation of electrodes to the pulse generator of the ventricular ATP pacing circuit 78 to create a virtual electrode for treatment of the tachycardia. The identification of a VT focus and the creation of a virtual electrode thus provide an improvement in the effectiveness of the therapy delivered for the particular arrhythmia.

Figure 5:
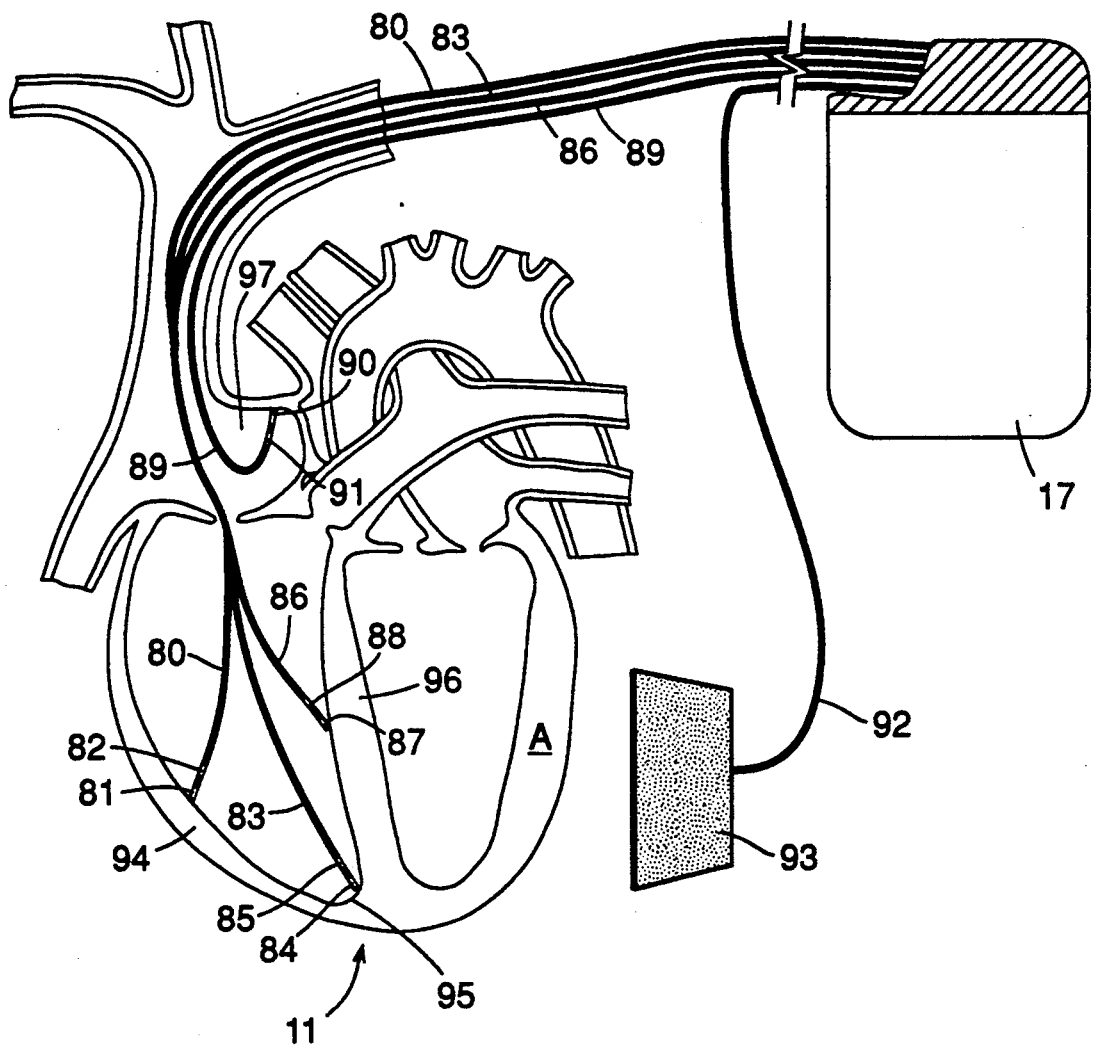
FIG. 5. illustrates in diagrammatic form a number of possible electrode orientations, relative to a heart, which may be utilized in the ACS of FIG. 1; and, FIGS. 6A-6F show examples of different types of electrodes which may be used in accordance with the present invention.

Referring now to FIG. 5, a number of possible electrode orientations that may be selected by the sensing circuitry 70 of FIG. 4 to establish a virtual electrode and apply appropriate ATP therapy in accordance with one embodiment of the present invention will now be considered. In the embodiment illustrated, four multielectrode endocardial catheters or leads 80, 83, 86 and 89 are utilized in conjunction with a subcutaneous patch lead 92 and/or the can of pacemaker 17 both to provide sensing information to the pacemaker from the heart 11 and to provide pacing pulses from the pacemaker to the heart. Lead 80 is provided with respective conventional distal tip and ring electrodes 81 and 82; lead 83 is provided with respective conventional distal tip and ring electrodes 84 and 85; lead 86 is provided with respective conventional distal tip and ring electrodes 87 and 88; lead 89 is provided with respective conventional distal tip and ring electrodes 90 and 91; and, lead 92 is provided with a conventional subcutaneous patch electrode 93.

The distal end of lead 80 is preferably anchored to the right free wall 94 of the heart by conventional means (tines, lead screws, or the like). Similarly, the distal end of lead 83 is preferably anchored to the apex 95 the right ventricle of the heart; the distal end of lead 86 is preferably anchored to the right septal wall 96 of the heart; and the distal end of lead 89 is preferably anchored in the high right atrium 97 of the heart.

Assuming that the sensing circuitry 70 (FIG. 4) has determined that a VT focus exists at point "A" in the FIG. 5 embodiment, the circuitry 70 determines the order of closeness to point "A" of the electrodes 81, 82, 84, 85, 87, 88, 90, 91, 93 and the pacemaker can and, for the embodiment illustrated, utilizes an appropriate one (for example, Orientation No. 2) of the twenty-two representative electrode orientations shown in Table I, below, to establish a virtual electrode and apply appropriate antitachycardia pacing therapy to the patient:

conventional patches may be used for the functions of pacing and sensing.

The antitachycardia pacing therapy provided by the present invention may take the form of either synchronous or non-synchronous waves, and the latter may have a predetermined phase difference. Also, the antitachycardia pacing therapy may be in the form of pacing waves having differing amplitudes, such differing amplitudes preferably being established as a function of the amplitudes of the waveform at its fiducial points.

It will be apparent from the foregoing description that the present invention provides an improved antitachycardia pacing device and method in which three or more sensing electrodes and a sensing circuit are

TABLE I

| ORIENTATION | ELECTRODE | POLARITY | ELECTRODE | POLARITY | PATCH | POLARITY | REFERENCE |
|---|---|---|---|---|---|---|---|
| 1 | 84 | + | 85 | + | 93 | − | Can |
| 2 | 84 | + | 87 | + | 93 | − | Can |
| 3 | 84 | + | 88 | + | 93 | − | Can |
| 4 | 84 | + | 81 | + | 93 | − | Can |
| 5 | 84 | + | 82 | + | 93 | − | Can |
| 6 | 85 | + | 87 | zero | 93 | − | Electr. 87 |
| 7 | 85 | + | 88 | + | 93 | − | Can |
| 8 | 85 | + | 81 | + | 93 | − | Can |
| 9 | 85 | + | 82 | + | 93 | − | Can |
| 10 | 87 | + | 88 | zero | 93 | − | Electr. 88 |
| 11 | 87 | + | 81 | + | 93 | − | Can |
| 12 | 87 | + | 82 | + | 93 | − | Can |
| 13 | 88 | + | 81 | + | 93 | − | Can |
| 14 | 88 | + | 82 | + | 93 | − | Can |
| 15 | 81 | + | 82 | + | 93 | − | Can |
| 16 | 84 | + | 85 | − | 93 | zero | Patch |
| 17 | 84 | + | 87 | − | 93 | zero | Patch |
| 18 | 84 | + | 88 | − | 93 | zero | Patch |
| 19 | 84 | + | 88 | − | 93 | zero | Patch |
| 20 | 84 | + | 81 | − | 93 | zero | Patch |
| 21 | 84 | + | 82 | − | 93 | zero | Patch |
| 22 | 85 | + | 87 | − | 93 | zero | Patch |

The twenty-two orientations shown in Table I, above, are intended to be representative of, rather than limiting to, the number of different orientations that may be employed.

Referring now to FIGS. 6A-6F, the electrode configurations employed for sensing and pacing may take different forms, including a mixture of conventional leads plus additional multifilar, multi-electrode leads. The additional multi-electrode leads can be of several endocardial forms, such as the "right ventricular J" lead 100 shown in FIG. 6A, which is provided with electrodes 101-103 and a coaxial three-terminal connector 104; the "anchor" lead 105 shown in FIG. 6B, which is provided with electrodes 106-109 and a suitable multi-terminal connector (not shown); the "umbrella" lead 110 shown in FIG. 6C, which is provided with electrodes 111-116 and a corresponding connector (not shown); the "egg beater" lead 117 shown in FIG. 6D, which is provided with electrodes 118-121 and a corresponding connector (not shown); and, the "spiral" lead 122 shown in FIG. 6E, which is provided with electrodes 123-127 and a corresponding connector (not shown). In addition, as shown in FIG. 6F, pacing/sensing leads such as lead 128 may be attached to epicardial or subcutaneous patches, such as patch 129, which may be provided with a supplemental silicone or polyurethane wing patch 130. Wing patch 130 is employed to provide increased spacing between the electrodes 131-134, which electrodes are preferably fixed to the wing patch. In alternative embodiments employed to endocardially identify the focus site of a tachycardia and to create a virtual electrode utilizing a selected orientation of the sensing electrodes, and in which a voltage of suitable level is applied to the oriented electrodes to establish an electrical field at the focus site having a greater field strength than the stimulation threshold of cardiac tissue at such site.

In testing one embodiment of the invention, VT's were induced in the hearts of dogs and a hand-held mapping probe was used to map the heart in each instance. The number of electrodes available was restricted to three. Nevertheless, the experimentation showed that antitachycardia pacing at the electrodes closest to the arrhythmia focus was more effective than pacing at the traditional right ventricular apex site in terminating the arrhythmia.

While there have been shown and described what are presently considered to be the preferred embodiments of this invention, it will be obvious to those skilled in the art that various other changes and modifications may be made without departing from the broader aspects of the invention. It is, therefore, aimed in the appended claims to cover all such changes and modifications as fall within the true spirit and scope of the invention.

What is claimed is:

1. An implantable device for treating cardiac arrhythmias in a patient's heart, comprising:
    detecting means for detecting a tachycardia having a site of focus in the heart;

an electrode system including at least three electrodes for delivering antitachycardia pacing therapy to the heart;

means for determining the relative distances of said electrodes from said tachycardia focus site;

antitachycardia pacing therapy means for supplying antitachycardia pacing therapy to said electrodes;

orienting means responsive to said relative distances determining means for connecting at least three selected ones of said at least three electrodes to said antitachycardia pacing therapy means in such a manner as to create a virtual electrode at or near said tachycardia focus site when said antitachycardia pacing therapy is supplied to said selected electrodes; and, means operative when said selected electrodes have been connected to said antitachycardia pacing therapy means for actuating said antitachycardia pacing therapy means to supply said antitachycardia pacing therapy to said selected electrodes.

2. A device according to claim 1, wherein said orienting means connects at least two of said selected electrodes to receive electrical charges. and a third one of said selected electrodes to serve as a reference electrode during the delivery of antitachycardia pacing therapy to the heart.

3. A device according to claim 2, wherein said electrode system also serves to sense electrical signals in the heart, and wherein said detecting means is coupled to said electrode system.

4. A device according to claim 3, wherein at least one of said at least two of said selected electrodes connected to receive electrical charges comprises an endocardial electrode.

5. A device according to claim 3, wherein said at least two of said selected electrodes connected to receive electrical charges comprise endocardial electrodes.

6. A device according to claim 3, wherein at least one of said at least two of said selected electrodes connected to receive electrical charges is an epicardial electrode.

7. A device according to claim 2, wherein at least one of said at least two of said selected electrodes connected to receive electrical charges comprises an endocardial electrode.

8. A device according to claim 7, wherein at least one of said at least two of said selected electrodes connected to receive electrical charges is an epicardial electrode.

9. A device according to claim 2, wherein said at least two of said selected electrodes connected to receive electrical charges comprise endocardial electrodes.

10. A device according to any one of claims 3–9, wherein said reference electrode is other than an endocardial electrode.

11. A device according to any one of claims 3–9, wherein said reference electrode is an epicardial patch electrode.

12. A device according to any one of claims 3–9, wherein said reference electrode is a subcutaneous patch electrode.

13. A device according to any one of claims 3–9, wherein said device includes an outer case having a conductive outer surface on at least a portion thereof, wherein said outer case is adapted to be positioned subcutaneously in the patient, and wherein said conductive outer surface of said case comprises said reference electrode.

14. A device according to any one of claims 3–9, wherein said antitachycardia pacing therapy means provides said antitachycardia pacing therapy in the form of synchronous pacing waves which approach the focus site from different directions.

15. A device according to claim 14, wherein said orienting means identifies fiducial points on a waveform of the heart and examines the relative timing of said fiducial points to determine said three selected ones of said at least three electrodes.

16. A device according to any one of claims 3–9, wherein said antitachycardia pacing therapy means provides said antitachycardia pacing therapy in the form of non-synchronous pacing waves which approach the focus site from different directions.

17. A device according to claim 16, wherein said orienting means identifies fiducial points on a waveform of the heart and examines the relative timing of said fiducial points to determine said three selected ones of said at least three electrodes.

18. A device according to claim 16, wherein said antitachycardia pacing therapy means provides non-synchronous pacing waves having a predetermined phase difference.

19. A device according to any one of claims 3–9, wherein said antitachycardia pacing therapy means provides said antitachycardia pacing therapy in the form of pacing waves having differing amplitudes.

20. A device according to claim 19, wherein said orienting means identifies fiducial points on a waveform of the heart and examines the relative amplitudes of the waveform at said fiducial points to determine said three selected ones of said at least three electrodes.

21. A device according to claim 20, further including means for determining said differing amplitudes as a function of the amplitudes of the waveform at said fiducial points.

22. A method of treating cardiac arrhythmias in a patient's heart, comprising the steps of:

providing an electrode system including at least three electrodes for delivering antitachycardia pacing therapy to the heart;

providing a source of antitachycardia pacing therapy for supplying antitachycardia pacing therapy to said electrodes;

detecting a tachycardia having a site of focus in the heart;

determining the relative distances of said electrodes from said tachycardia focus site;

connecting at least three selected ones of said at least three electrodes to said source of antitachycardia pacing therapy based on said relative distances determination and in such a manner as to create a virtual electrode at said tachycardia focus site during the delivery of said antitachycardia pacing therapy to the heart; and, delivering said antitachycardia pacing therapy to said selected electrodes.

23. A method according to claim 22, wherein said step of connecting at least three selected ones of said at least three electrodes to said source of antitachycardia pacing therapy includes the substep of connecting at least two of said electrodes to receive electrical charges during the delivery of antitachycardia pacing therapy to the heart and connecting a third one of said electrodes to serve as a reference electrode during the delivery of antitachycardia pacing therapy to the heart.

24. A method according to claim 23, wherein said step of detecting a tachycardia includes the sub-step of utilizing said electrode system to sense electrical signals in the heart.

25. A method according to any one of claims 22–24, wherein said step of delivering said antitachycardia pacing therapy includes the sub-step of delivering said antitachycardia pacing therapy in the form of simultaneous pacing waves which approach the focus site from different directions.

26. A method according to claim 25, wherein said step of determining the relative distances of said electrodes from the focus site includes the sub-steps of identifying fiducial points on a waveform of the heart and examining the relative timing of said fiducial points.

27. A method according to claim 25, wherein said step of determining the relative distances of said electrodes from the focus site includes the sub-steps of identifying fiducial points on a waveform of the heart and examining the relative amplitudes of said fiducial points.

28. A method according to claim 25, wherein said step of determining the relative distances of said electrodes from the focus site includes the sub-steps of identifying fiducial points on a waveform of the heart and examining the relative timing and amplitudes of said fiducial points.

* * * * *